(12) United States Patent  (10) Patent No.: US 7,597,103 B2
Thornton et al.  (45) Date of Patent: *Oct. 6, 2009

(54) DEVICE AND METHOD FOR IMPROVING A USER'S BREATHING

(75) Inventors: W. Keith Thornton, 5524 Edlen Dr., Dallas, TX (US) 75220-2106; Michael J. Zalta, Richardson, TX (US)

(73) Assignee: W. Keith Thornton, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/674,317

(22) Filed: Feb. 13, 2007

(65) Prior Publication Data

US 2007/0125388 A1  Jun. 7, 2007

Related U.S. Application Data

(63) Continuation of application No. 10/428,904, filed on May 1, 2003, now Pat. No. 7,174,895.

(60) Provisional application No. 60/376,746, filed on May 1, 2002.

(51) Int. Cl.
*A61F 5/56* (2006.01)
*A61C 5/14* (2006.01)
*A61C 3/00* (2006.01)
*A61C 9/00* (2006.01)
*A61C 5/00* (2006.01)

(52) U.S. Cl. .............. 128/848; 128/857; 128/859; 128/861; 433/6; 433/19; 433/42; 433/215

(58) Field of Classification Search ............ 128/848, 128/857, 859, 861; 433/6, 19, 42, 215
See application file for complete search history.

(56) References Cited

U.S. PATENT DOCUMENTS 690,663 A    1/1902  Pratt
746,869 A   12/1903  Moulton (Continued)

FOREIGN PATENT DOCUMENTS

DE        2 320 501       11/1974

(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner*—Patricia Bianco
*Assistant Examiner*—Tarla Patel
(74) *Attorney, Agent, or Firm*—Baker Botts L.L.P.

(57) ABSTRACT

In one embodiment, a device for improving a user's breathing includes an upper arch adapted to receive at least some of the user's upper teeth and a lower arch adapted to receive at least some of the user's lower teeth. A hook having an end is coupled to the upper arch. The lower arch includes a recess adapted to receive and position the end of the hook to pull the lower arch forward to facilitate improved breathing.

11 Claims, 6 Drawing Sheets

U.S. PATENT DOCUMENTS

| | | |
|---|---|---|
| 774,446 A | 11/1904 | Moulton |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper .................. 32/19 |
| 2,178,128 A | 10/1939 | Waite .................. 128/136 |
| 2,424,533 A | 7/1947 | Faires .................. 128/136 |
| 2,505,028 A | 4/1950 | Boeger .................. 128/215 |
| 2,521,039 A | 9/1950 | Carpenter .................. 128/136 |
| 2,521,084 A | 9/1950 | Oberto .................. 128/141 |
| 2,531,222 A | 11/1950 | Kesling .................. 32/14 |
| 2,574,623 A | 11/1951 | Clyde .................. 128/136 |
| 2,590,118 A | 3/1952 | Oddo, Jr. .................. 128/136 |
| 2,627,268 A | 2/1953 | Leppich .................. 128/136 |
| 2,833,278 A | 5/1958 | Ross .................. 128/136 |
| 2,867,212 A | 1/1959 | Nunn, Jr. .................. 128/136 |
| 2,882,893 A | 4/1959 | Godfroy .................. 128/136 |
| 3,037,501 A | 6/1962 | Miller .................. 128/141 |
| 3,064,354 A | 11/1962 | Pos .................. 32/19 |
| 3,107,668 A | 10/1963 | Thompson .................. 128/136 |
| 3,124,129 A | 3/1964 | Grossberg .................. 128/136 |
| 3,132,647 A | 5/1964 | Corniello .................. 128/136 |
| 3,219,033 A | 11/1965 | Wallshein .................. 128/136 |
| 3,277,892 A | 10/1966 | Tepper .................. 128/172.1 |
| 3,312,216 A | 4/1967 | Wallshein .................. 128/136 |
| 3,321,832 A | 5/1967 | Weisberg .................. 32/32 |
| 3,360,860 A | 1/1968 | Roland .................. 32/17 |
| 3,434,470 A | 3/1969 | Strickland .................. 128/136 |
| 3,457,916 A | 7/1969 | Wolicki .................. 128/136 |
| 3,513,838 A | 5/1970 | Foderick, et al. .................. 128/136 |
| 3,522,805 A | 8/1970 | Wallshein .................. 128/136 |
| 3,690,004 A | 9/1972 | Frush .................. 32/17 |
| 3,854,208 A | 12/1974 | Arant .................. 32/19 |
| 3,864,832 A | 2/1975 | Carlson .................. 32/40 R |
| 3,871,370 A | 3/1975 | McDonald .................. 128/136 |
| 3,882,601 A | 5/1975 | Jahn .................. 32/17 |
| 3,884,226 A | 5/1975 | Tepper .................. 128/136 |
| 4,016,650 A | 4/1977 | Leusner et al. .................. 32/17 |
| 4,026,024 A | 5/1977 | Tradowsky .................. 32/19 |
| 4,114,614 A | 9/1978 | Kesling .................. 128/136 |
| 4,169,473 A | 10/1979 | Samelson .................. 128/136 |
| 4,182,312 A | 1/1980 | Mushabac .................. 433/68 |
| 4,227,877 A | 10/1980 | Tureaud et al. .................. 433/37 |
| 4,289,127 A | 9/1981 | Nelson .................. 128/207.14 |
| 4,304,227 A | 12/1981 | Samelson .................. 128/136 |
| 4,376,628 A | 3/1983 | Aardse .................. 433/80 |
| 4,382,783 A | 5/1983 | Rosenberg .................. 433/19 |
| 4,433,956 A | 2/1984 | Witzig .................. 433/7 |
| 4,439,147 A | 3/1984 | Magill et al. .................. 433/3 |
| 4,439,149 A | 3/1984 | Devincenzo .................. 433/6 |
| 4,454,090 A | 6/1984 | Saumell .................. 264/154 |
| 4,495,945 A | 1/1985 | Liegner .................. 128/200.26 |
| 4,505,672 A | 3/1985 | Kurz .................. 433/6 |
| 4,530,662 A | 7/1985 | Andersson et al. .................. 433/37 |
| 4,553,549 A | 11/1985 | Pope et al. .................. 128/421 |
| 4,568,280 A | 2/1986 | Ahlin .................. 433/6 |
| 4,569,342 A | 2/1986 | von Nostitz .................. 128/136 |
| 4,593,686 A | 6/1986 | Lloyd et al. .................. 128/136 |
| 4,602,905 A | 7/1986 | O'Keefe, III .................. 433/41 |
| 4,639,220 A | 1/1987 | Nara et al. .................. 433/69 |
| 4,668,188 A | 5/1987 | Wolfenson et al. .................. 433/37 |
| 4,669,459 A | 6/1987 | Spiewak et al. .................. 128/136 |
| 4,676,240 A | 6/1987 | Gardy .................. 128/207.14 |
| 4,715,368 A | 12/1987 | George .................. 128/136 |
| 4,773,853 A | 9/1988 | Kussick .................. 433/6 |
| 4,784,123 A | 11/1988 | Robeson .................. 128/90 |
| 4,799,500 A | 1/1989 | Newbury .................. 128/859 |
| 4,862,903 A | 9/1989 | Campbell .................. 128/861 |
| 4,892,478 A | 1/1990 | Tateosian et al. .................. 433/6 |
| 4,901,737 A | 2/1990 | Toone .................. 128/848 |
| 4,932,867 A | 6/1990 | Ueno .................. 433/69 |
| 4,955,393 A | 9/1990 | Adell .................. 128/859 |
| RE33,442 E | 11/1990 | George .................. 128/860 |
| 5,003,994 A | 4/1991 | Cook .................. 128/848 |
| 5,011,407 A | 4/1991 | Pelerin .................. 433/48 |
| 5,018,533 A | 5/1991 | Hawkins .................. 128/848 |
| 5,026,278 A | 6/1991 | Oxman et al. .................. 433/41 |
| 5,028,232 A | 7/1991 | Snow .................. 433/24 |
| 5,040,976 A | 8/1991 | Ubel, III et al. .................. 433/41 |
| 5,042,506 A | 8/1991 | Liberati .................. 128/848 |
| 5,046,512 A | 9/1991 | Murchie .................. 128/848 |
| 5,052,409 A | 10/1991 | Tepper .................. 128/859 |
| 5,055,039 A | 10/1991 | Abbatte et al. .................. 433/24 |
| 5,056,534 A | 10/1991 | Wright .................. 128/848 |
| 5,064,371 A | 11/1991 | Smeltzer .................. 433/37 |
| 5,066,231 A | 11/1991 | Oxman et al. .................. 433/214 |
| 5,078,600 A | 1/1992 | Austin .................. 433/73 |
| 5,092,346 A | 3/1992 | Hays et al. .................. 128/848 |
| 5,103,838 A | 4/1992 | Yousif .................. 128/859 |
| 5,112,225 A | 5/1992 | Diesso .................. 433/48 |
| 5,117,816 A | 6/1992 | Shapiro et al. .................. 128/200.24 |
| 5,154,184 A | 10/1992 | Alvarez .................. 128/848 |
| 5,154,609 A | 10/1992 | George .................. 433/68 |
| 5,183,057 A | 2/1993 | Syrop et al. .................. 128/845 |
| 5,188,529 A | 2/1993 | Lüth .................. 433/68 |
| 5,190,457 A | 3/1993 | Schreinemakers .......... 433/214 |
| 5,213,498 A | 5/1993 | Pelerin .................. 433/37 |
| 5,267,862 A | 12/1993 | Parker .................. 433/215 |
| 5,277,202 A | 1/1994 | Hays .................. 128/848 |
| 5,284,161 A | 2/1994 | Karell .................. 128/848 |
| 5,313,960 A | 5/1994 | Tomasi .................. 128/848 |
| 5,316,020 A | 5/1994 | Truffer .................. 128/848 |
| 5,320,533 A | 6/1994 | Lee .................. 433/218 |
| 5,365,945 A | 11/1994 | Halstrom .................. 128/848 |
| 5,370,533 A | 12/1994 | Bushnell .................. 433/36 |
| 5,373,859 A | 12/1994 | Forney .................. 128/846 |
| 5,409,017 A | 4/1995 | Lowe .................. 128/848 |
| 5,415,544 A | 5/1995 | Oxman et al. .................. 433/48 |
| 5,427,117 A | 6/1995 | Thornton .................. 128/848 |
| 5,503,552 A | 4/1996 | Diesso .................. 433/37 |
| 5,537,994 A | 7/1996 | Thornton .................. 128/204.18 |
| 5,551,872 A | 9/1996 | Mena .................. 433/37 |
| 5,562,449 A | 10/1996 | Jacobs et al. .................. 433/215 |
| 5,566,683 A | 10/1996 | Thornton .................. 128/848 |
| 5,582,517 A | 12/1996 | Adell .................. 433/6 |
| 5,678,567 A | 10/1997 | Thornton et al. .................. 128/848 |
| 5,681,164 A | 10/1997 | Bass .................. 433/6 |
| 5,718,244 A | 2/1998 | Thornton .................. 128/864 |
| 5,720,302 A | 2/1998 | Belfer .................. 128/848 |
| 5,755,219 A | 5/1998 | Thornton .................. 128/201.18 |
| 5,807,100 A | 9/1998 | Thornton .................. 433/48 |
| 5,829,441 A * | 11/1998 | Kidd et al. .................. 128/848 |
| 5,846,082 A | 12/1998 | Thornton .................. 433/215 |
| 5,954,048 A | 9/1999 | Thornton .................. 128/201.18 |
| 5,983,892 A | 11/1999 | Thornton .................. 128/201.26 |
| 6,083,442 A | 7/2000 | Gabilly .................. 264/163 |
| 6,109,265 A | 8/2000 | Frantz et al. .................. 128/848 |
| 6,155,262 A | 12/2000 | Thornton et al. .................. 128/859 |
| 6,209,542 B1 | 4/2001 | Thornton .................. 128/206.29 |
| 6,247,926 B1 | 6/2001 | Thornton .................. 433/48 |
| 6,305,376 B1 | 10/2001 | Thornton .................. 128/848 |
| 6,318,997 B1 | 11/2001 | Mayweather .................. 433/45 |
| 6,325,064 B1 | 12/2001 | Thornton .................. 128/204.18 |
| 6,374,824 B1 | 4/2002 | Thornton .................. 128/201.26 |
| 6,405,729 B1 | 6/2002 | Thornton .................. 128/848 |

| | | | |
|---|---|---|---|
| 6,464,924 B1 | 10/2002 | Thornton | 264/331.12 |
| 6,516,805 B1 | 2/2003 | Thornton | 128/848 |
| 6,571,798 B1 | 6/2003 | Thornton | 128/206.21 |
| 6,675,802 B1 | 1/2004 | Thornton | 128/206.29 |
| 6,845,774 B2 * | 1/2005 | Gaskell | 128/848 |
| 6,877,513 B2 | 4/2005 | Scarberry et al. | 128/848 |
| 7,174,895 B2 * | 2/2007 | Thornton et al. | 128/848 |
| 2002/0000230 A1 | 1/2002 | Gaskell | 128/848 |
| 2004/0237965 A1 | 12/2004 | Bibi et al. | 128/206.29 |

FOREIGN PATENT DOCUMENTS

| | | |
|---|---|---|
| DE | 29506512.5 | 7/1995 |
| EP | 0 312 368 A1 | 4/1989 |
| EP | 0 359 135 A1 | 3/1990 |
| GB | 1 569 129 | 6/1980 |
| GB | 2 072 567 A | 10/1981 |
| WO | WO 91/12777 | 9/1991 |
| WO | WO 98/26736 | 6/1998 |
| WO | WO 98/46177 | 10/1998 |

OTHER PUBLICATIONS

Photocopies of 2-piece dental device manufactured by Currie-Gibson Dental Laboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brouchure, 3 pages, unknown.

Great Lakes Orthodontics, Ltd.; *Nocturnal Airway Patency Appliance*; 2 pages, not dated.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

PCT Notification of Transmittal of The International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

Thornton, "Oral Appliance for Treating a Breathing Condition," Pending U.S. Appl. No. 11/278,918, 42 pages, filed Apr. 6, 2006.

Japanese Patent Office Action re: Japanese Patent Application No. 2004-500750; 4 pages, mailing date: Oct. 14, 2008.

* cited by examiner

DEVICE AND METHOD FOR IMPROVING A USER'S BREATHING

RELATED APPLICATIONS

This application is a continuation of U.S. application Ser. No. 10/428,904, filed May 1, 2003, now U.S. Pat. No. 7,174,895, which claims priority under 35 U.S.C. § 119 to Provisional Application No. 60/376,746, filed May 1, 2002.

TECHNICAL FIELD OF THE INVENTION

This invention relates generally to oral appliances, and more particularly to a device and method for improving a user's breathing.

BACKGROUND

Many people experience breathing problems, which may result in difficulty sleeping, in snoring, or in other more serious conditions such as obstructive sleep apnea. One treatment for such breathing disorders involves the use of devices that are inserted into a user's mouth for extending the user's lower jaw forward. These devices open the breathing passageway more fully to allow easier breathing through the nose and mouth. Certain of these devices include upper and lower arches that are connected together using a mechanism that may be adjusted to pull the lower arch, and thus the user's lower jaw, forward.

SUMMARY OF THE INVENTION

The device and method of the present invention may reduce or eliminate certain disadvantages and problems associated with previous devices and methods for improving breathing.

In one embodiment, a device for improving a user's breathing includes an upper arch adapted to receive at least some of the user's upper teeth and a lower arch adapted to receive at least some of the user's lower teeth. A hook having an end is coupled to the upper arch. The lower arch includes a recess adapted to receive and position the end of the hook to pull the lower arch forward to facilitate improved breathing.

In another embodiment, a hook for a device for improving a user's breathing is adapted to be coupled to an upper arch of the device for receiving at least some of the user's upper teeth. The hook includes an end adapted to be received and positioned within a recess of a lower arch of the device for receiving at least some of the user's lower teeth to pull the upper arch forward to facilitate improved breathing.

In another embodiment, a positioning mechanism for a device for improving a user's breathing is provided for positioning a lower arch that is adapted to receive at least some of a user's lower teeth. The positioning mechanism includes a hook adapted to be coupled to an upper arch that is adapted to receive at least some of the user's upper teeth. The hook includes an end. The positioning mechanism also includes a lower platform adapted to be coupled to the lower arch. The lower platform includes a recess adapted to receive and position the end of the hook to pull the lower arch forward to facilitate improved breathing.

Certain embodiments of the present invention may provide one or more technical advantages. For example, certain embodiments may allow the lower arch to be precisely positioned relative to the upper arch, while still allowing certain freedom of movement of the lower jaw. As another example, certain embodiments may allow the lower arch to be precisely positioned vertically relative to the upper arch to precisely determine the opening of the user's lower jaw. As another example, in certain embodiments the device, including a positioning mechanism, an adjustment mechanism, or both, may reside entirely within the user's mouth for improved comfort and usability. Certain embodiments may provide all, some, or none of these advantages. Certain embodiments may provide one or more other technical advantages, one or more of which may be readily apparent to those skilled in the art from the figures, description, and claims included herein.

BRIEF DESCRIPTION OF THE DRAWINGS

For a more complete understanding of the present invention and at least some of its advantages, reference is now made to the following description taken in conjunction with the accompanying drawings, in which.

DESCRIPTION OF EXAMPLE EMBODIMENTS

Figure 1:
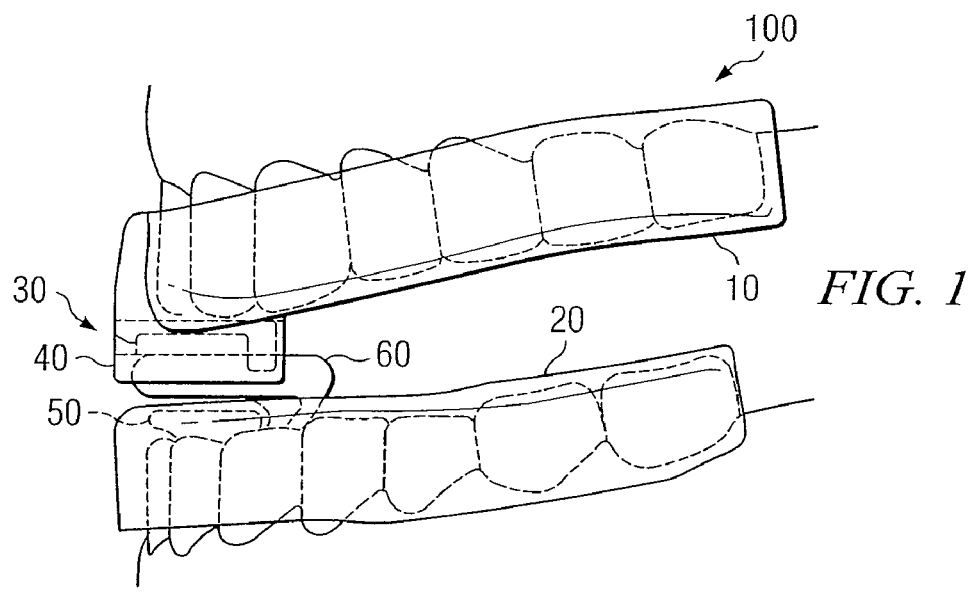
FIG. 1 illustrates a device for improving a user's breathing.
Figure 2:
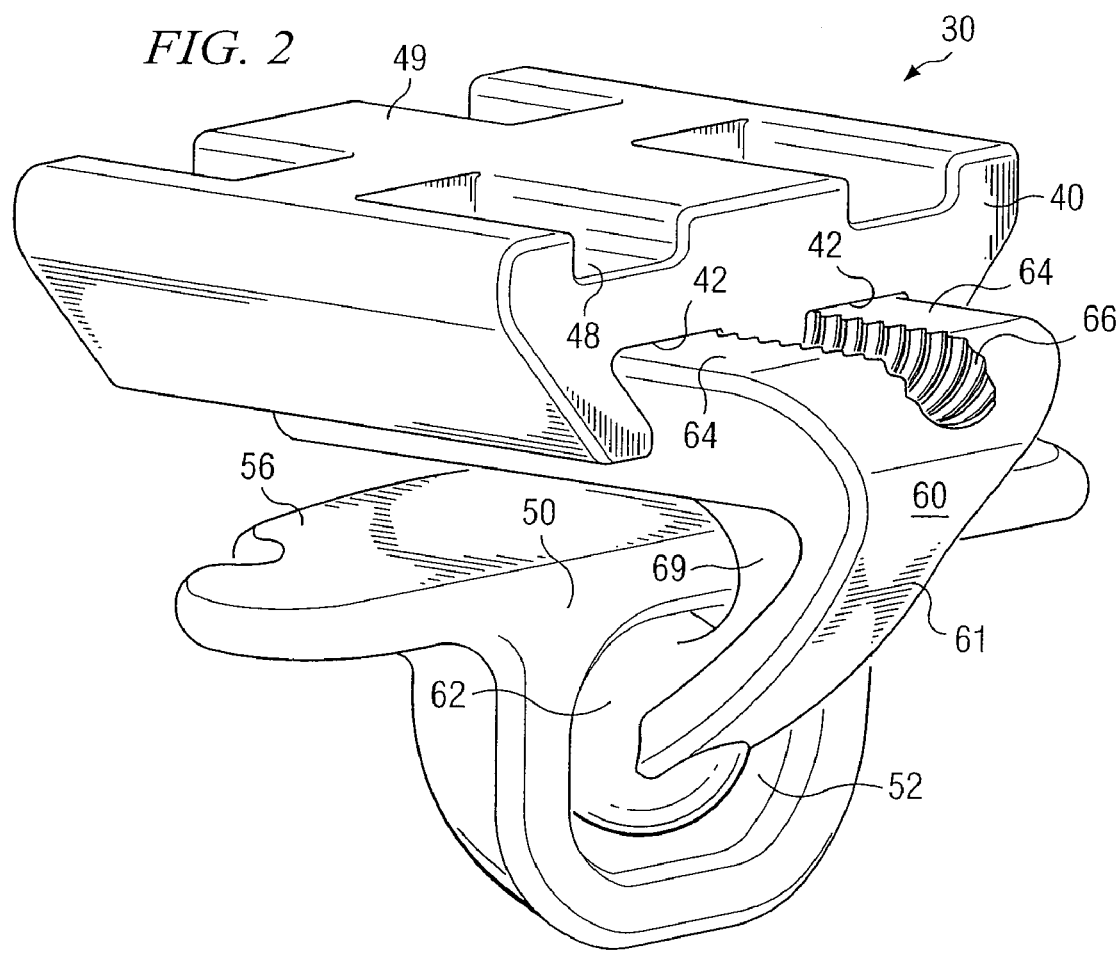
FIGS. 2 through 5 illustrate more detailed views of example vertical positioning and forward adjustment mechanisms.

FIG. 1 illustrates an example device 100 for improving a user's breathing. In general, device 100 may be used to treat sleep disordered breathing, such as snoring or obstructive sleep apnea, through forward adjustment of the user's lower jaw relative to the upper jaw. This opens the breathing passage and facilitates improved breathing through the user's nose and mouth. Preferably, device 100 remains entirely within the user's mouth and all surfaces of device 100 that may contact the interior of the user's mouth are smooth to prevent injury or discomfort.

Device 100 includes an upper arch 10 adapted to receive at least some of a user's upper teeth and a lower arch 20 adapted to receive at least some of the user's lower teeth. Upper arch 10 and lower arch 20 may include molds of at least some of the user's upper and lower teeth, respectively, for improved fitting, performance, and comfort. In one embodiment, device 100 includes a positioning and adjustment mechanism 30 that couples lower arch 20 to upper arch 10, positions lower arch 20 vertically relative to upper arch 10, and may be adjusted to pull lower arch 20 forward to facilitate improved breathing. In a more particular embodiment, lower arch 20 may be precisely positioned vertically relative to upper arch 10 to precisely determine the opening of the user's lower jaw. As described more fully below, mechanism 30 may include an upper platform 40 coupled to upper arch 10, a lower platform 50 coupled to lower arch 20, and a hook 60 coupling upper platform 40 to lower platform 50. These components may be made from any suitable material, for example, a biocompatible metal or hard plastic.

FIGS. 2 through 5 illustrate more detailed views of example vertical positioning and forward adjustment mechanisms associated with mechanism 30. Hook 60 and lower platform 50 preferably have cooperating shapes to position lower arch 20 relative to upper arch 10. End 62 of hook 60 may snap, click, or otherwise lock into recess 52 of lower platform 50, such that suitable force is needed to remove end 62 from recess 52, or end 62 may be freely removable from recess 52. In one embodiment, the cooperating shapes of lower platform 50 and hook 60 precisely position lower arch 20 vertically relative to upper arch 10 to precisely determine an opening of the user's lower jaw. Hook 60 and lower platform 50 may be collectively referred to as a vertical positioning mechanism for lower arch 20. In one embodiment, a substantially rounded recess 52 formed in lower platform 50 acts as a socket to receive a substantially rounded end 62 of hook 60. Recess 52 of lower platform 50 is adapted to receive and position end 62 of hook 60 to pull lower arch 20 forward to facilitate improved breathing. Substantially rounded end 62 of hook 60 may be substantially spherical, as shown, or may have any other suitable substantially rounded shape. Use of the modifier "substantially" is intended to make it clear that true mathematical roundness, as in a true circle or sphere, is not required and that a substantially rounded end 62 or a substantially rounded recess 52 may have any suitable curved profiles. Furthermore, although a substantially rounded end 62 and a substantially rounded recess 52 are primarily described and may be preferred in certain circumstances, the present invention contemplates any suitable cooperating shapes for end 62 and recess 52 depending on the embodiment. Lower platform 50 may be fully integral to, permanently coupled to, or separate and removable from lower arch 20. Unless otherwise clear from the context, lower platform 50 may be deemed a part of lower arch 20, whether or not lower platform 50 is integral to lower arch 20, such that lower arch 20 may be said to include recess 52.

In one embodiment, hook 60 may be modified according to particular needs to provide increased flexibility. For example, the anterior portion of hook 60 may be lengthened or otherwise modified, either during or after initial construction of hook 60, to provide a support arm for the attachment of a suitable continuous positive airway pressure (CPAP) apparatus. As another example, flange 64 of hook 60 may be lengthened, either during or after initial construction of hook 60, such that the maximum forward adjustment of the lower jaw is increased. In one embodiment, hook 60 may be selected from among multiple interchangeable hooks 60 having different lengths of arm 61 to customize device 100 according to particular needs. Depending upon the length of arm 61 of the particular hook 60 selected, a corresponding precise opening of the user's lower jaw may be determined.

Figure 3:
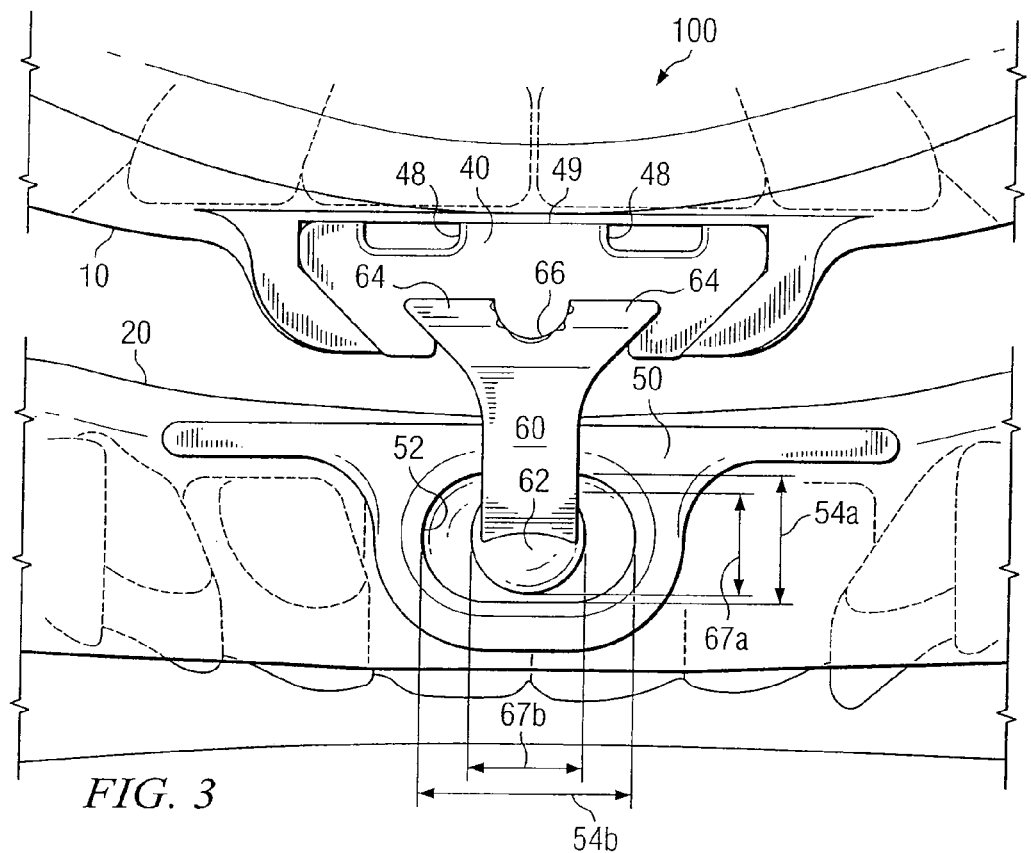
Figure 4:
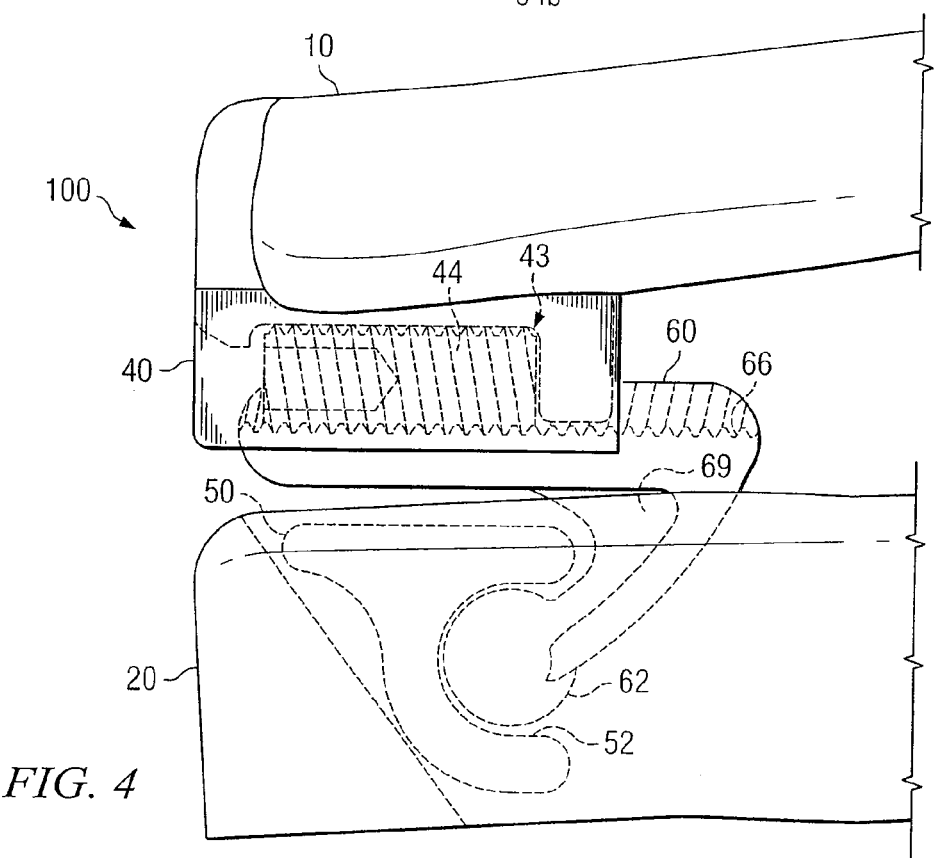

Referring to FIG. 3, in one embodiment a substantially rounded recess 52 of lower platform 50 is elongated such that substantially rounded recess 52 has a greater width than length, resulting in a substantially elliptical, ovular, or "pill" shape. In a particular embodiment, height 54a of substantially rounded recess 52 is slightly larger than height 67a of substantially rounded end 62 of hook 60, while width 54b of substantially rounded recess 52 is significantly larger than width 67b of substantially rounded end 62. Consequently, in this embodiment, lower platform 50, lower arch 20, and thus the user's lower jaw are permitted substantially more lateral freedom of movement than vertical freedom of movement, which may provide increased comfort without sacrificing performance associated with precise vertical positioning of lower arch 20. Similar elongation may be provided in embodiments in which end 62 and recess 52 are not substantially rounded. Where enhanced lateral freedom of movement for the lower jaw is not desired, any difference between widths 54b and 67b may be reduced. Of course, if no freedom of movement is desired vertically or laterally, then heights 54a and 67a or widths 54b and 67b, respectively, may be substantially equal. In one embodiment, a plate, strap, or other cover may be provided to secure end 62 in recess 52 to keep device 100 together during shipment, during use, between uses, or for any other suitable purposes.

Upper platform 40 may be fully integral to, permanently coupled to, or separate and removable from upper arch 10. For example, in one embodiment, upper arch 10 may include a slot to receive and engage upper platform 40 to couple upper platform 40 to upper arch 10, the slot and upper platform 40 having cooperating shapes. Although the slot of upper arch 10 and upper platform 40 are illustrated as being substantially triangular in shape along their sides, the slot of upper arch 10 and upper platform 40 may have any suitable cooperating shapes. Unless otherwise clear from the context, upper platform 40 may be deemed a part of upper arch 10, whether or not upper platform 40 is integral to upper arch 10.

In one embodiment, upper platform 40 may include a slot 42 to receive and engage a flange 64 of hook 60 to couple hook 60 to upper platform 40 and to allow forward and rearward adjustment of hook 60 to facilitate positioning of lower arch 20 and thus the user's lower jaw. Although slot 42 and flange 64 are illustrated as being substantially triangular in shape along their sides, slot 42 and flange 64 may have any suitable cooperating shapes.

In one embodiment, upper platform 40 includes a channel 43 that houses a threaded adjustor 44 and hook 60 includes a threaded channel 66 that engages the threads of adjustor 44. Adjustor 44 may be, for example, a threaded rod and may be made from any suitable material, for example, a biocompatible metal or hard plastic. Rotating adjustor 44, which is preferably prevented from moving forward or rearward within channel 43 using appropriate stops, causes hook 60 to move forwardly or rearwardly within slot 42 of upper platform 40.

Figure 5:
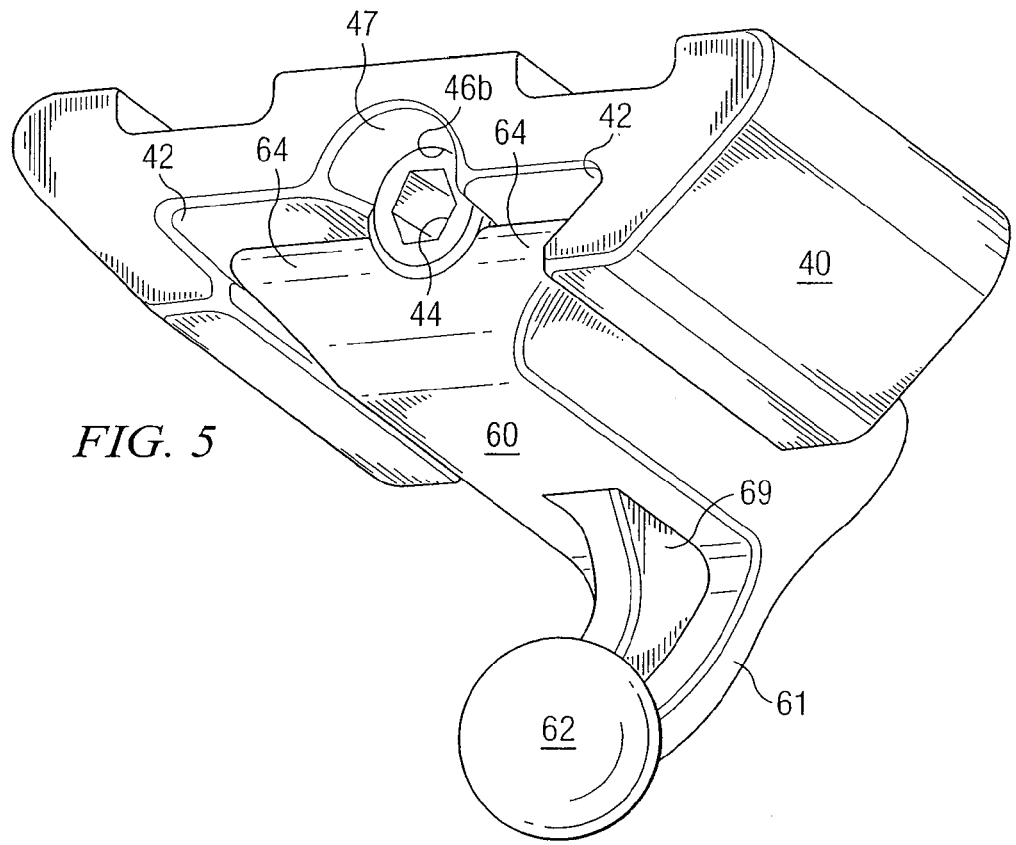

Referring to FIG. 5, in one embodiment upper platform 40 includes a stop 46b that substantially prevents adjustor 44 from moving forward when adjustor 44 is disposed in channel 43. A similar stop substantially preventing adjustor 44 from moving rearward is described below with reference to FIG. 7A. Upper platform 40 may include a depression 47 anterior to stop 46b to guide an Allen wrench or other suitable adjustment tool into a hexagonal or other recess formed in adjustor 44 to facilitate rotation of adjustor 44. Upper platform 40, adjustor 44, and hook 60 may be collectively referred to as a forward adjustment mechanism for lower arch 20.

The cooperating shapes of slot 42 of upper platform 40 and flange 64 of hook 60 permit forward and rearward travel of hook 60 within slot 42 while substantially preventing lateral and vertical movement of hook 60 relative to upper platform 40. Preferably, hook 60 is permitted to travel within slot 42 to any appropriate extent to adjust the extent to which lower arch 20, and thus the user's lower jaw, is pulled forward. For example, a portion of hook 60, including some or all of end 62, may be permitted to travel forward past the most anterior portion of upper platform 40 if desired, and a portion of hook 60, including some or all of end 62, may be permitted to travel rearward past the most posterior portion of upper platform 40 if desired, according to rotation of adjustor 44. However, as described more fully below, one or more stops may be provided to limit the forward and rearward travel of hook 60 within slot 42.

Figure 6A:
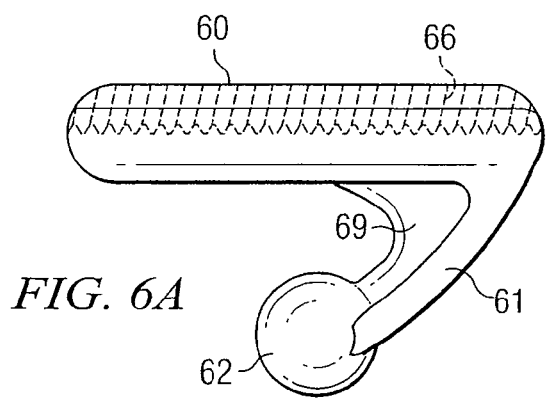
FIGS. 6A and 6B illustrate an example hook.
Figure 6B:
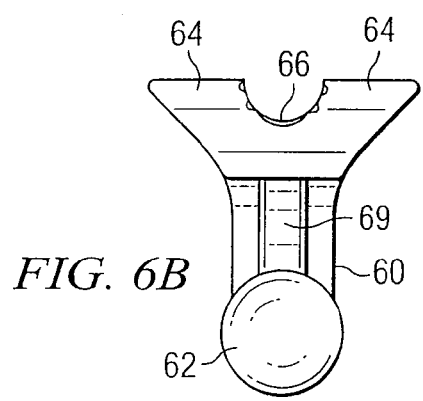
Figure 8A:
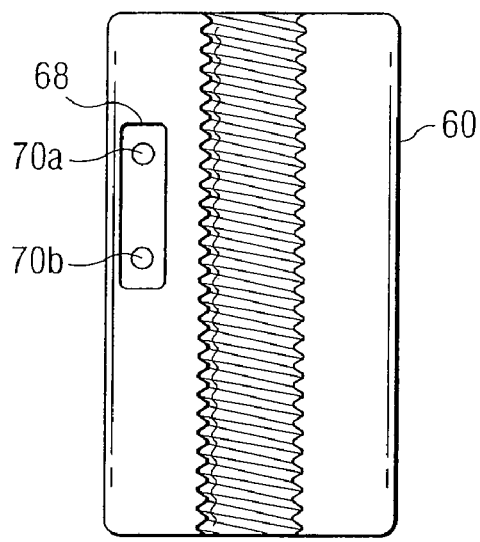
FIGS. 8A through 8C illustrate an example adjustment mechanism incorporating stops.

FIGS. 6A and 6B illustrate an example hook. In one embodiment, as described more fully below with reference to FIGS. 8A though 8C, one or more slots, cut-outs, or other elongated recesses 68 may be formed in flange 64 to contact one or more stops 70 that are positioned within upper platform 40 and made to extend into the one or more recesses 68 to limit the forward and rearward travel of hook 60 within slot 42 of upper platform 40. Hook 60 may include a flange 69 that provides additional strength to prevent deformation of hook 60 during use.

Figure 7A:
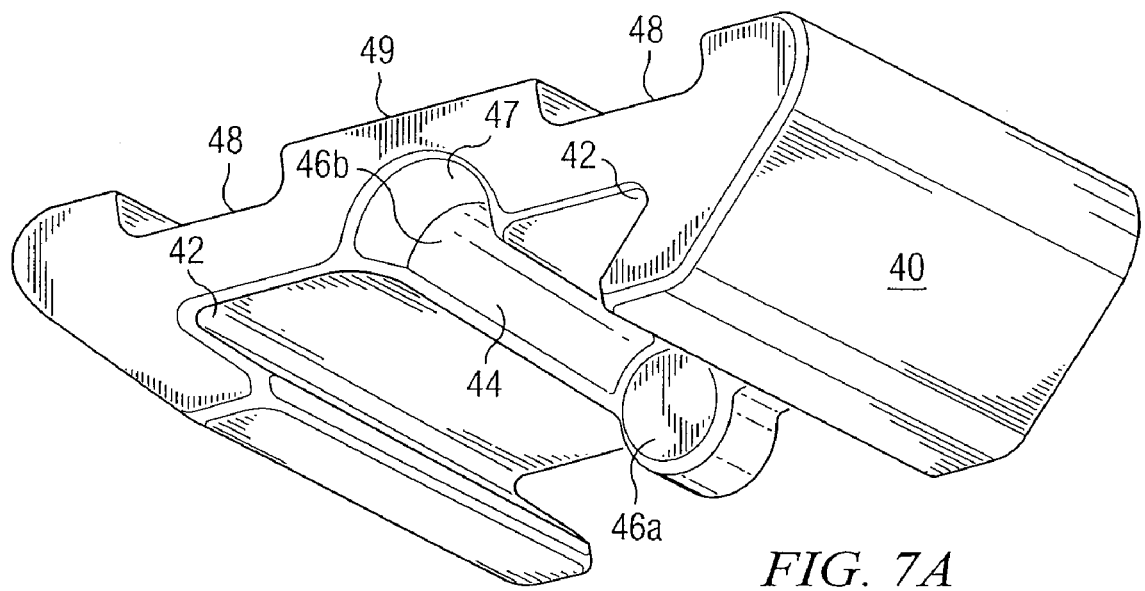
FIGS. 7A and 7B illustrate an example upper platform.
Figure 7B:
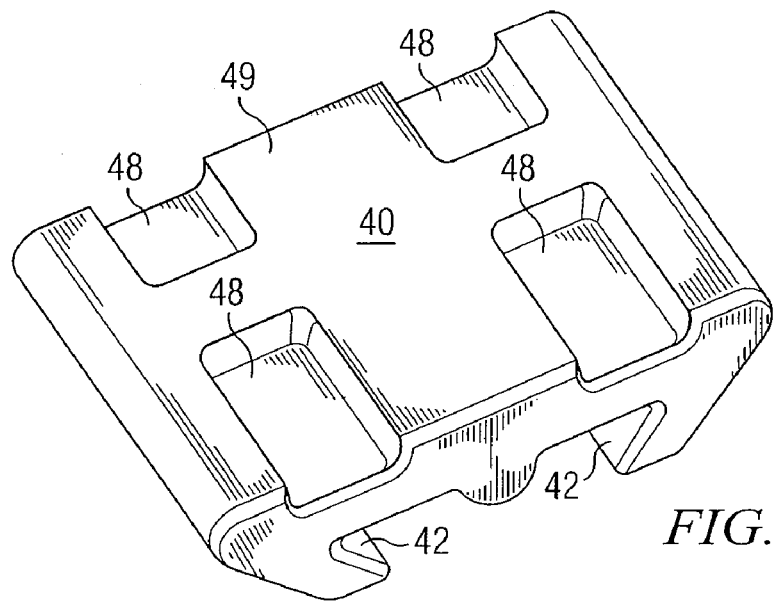

FIGS. 7A and 7B illustrate an example upper platform 40. As shown in FIG. 7A, in one embodiment channel 43, which houses threaded adjustor 44, is not threaded and adjustor 44 rotates freely within channel 43. Similar to stop 46b described above, stop 46a substantially prevents adjustor 44 from moving rearwardly when adjustor 44 is disposed in channel 43. As shown in FIG. 7B, in one embodiment upper platform 40 may include recesses 48 to receive a bonding material, such as an acrylic or adhesive, that helps couple upper platform 40 to upper arch 10. Middle portion 49 of upper platform 40 preferably adds additional thickness to upper platform 40 above adjustor 44 to provide strength.

Figure 8B:
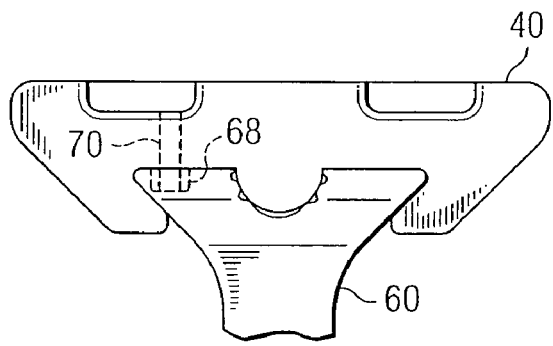
Figure 8C:
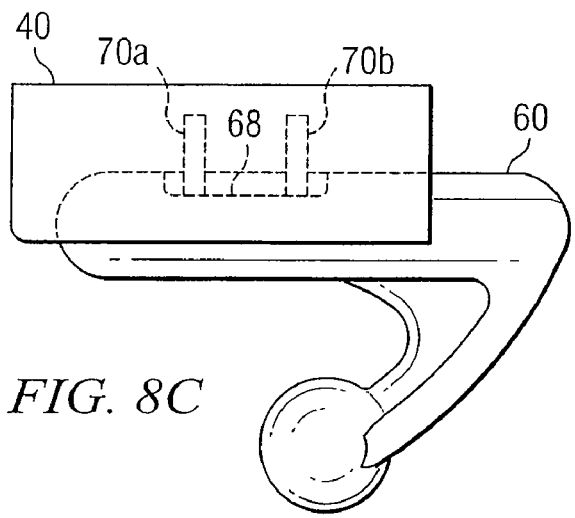

Referring to FIGS. 8B though 8C, in one embodiment, as described above, one or more stops 70 may be positioned within upper platform 40 and made to extend into one or more slots, cut-outs, or other elongated recesses 68 formed in flange 64 of hook 60 to limit the forward and rearward travel of hook 60 within slot 42. For example, stops 70 may be set screws placed in through-holes that are formed in upper platform 40. Either end of a recess 68 contacting a stop 70 will prevent further travel of hook 60 in a corresponding direction. In a particular embodiment, stops 70 may include a forward stop 70a for limiting the rearward travel of hook 60 within a single slot 42 and a rearward stop 70b for limiting the forward travel of hook 60 within the single slot 42. Although recess 68 is shown formed on the top of flange 64 of hook 60, recess 68 may be formed in any suitable location, for example, horizontally through either side of flange 64. Correspondingly, stops 70 may be positioned in any suitable location, for example, in through-holes formed in the sides of upper platform 40 to engage recess 68 formed horizontally through a side of flange 64.

Figure 9A:
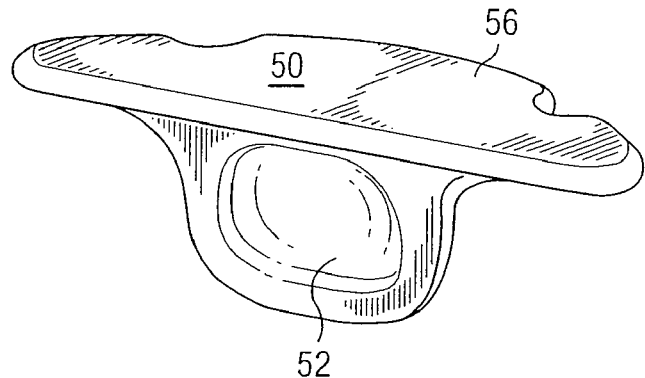
FIGS. 9A and 9B illustrate an example lower platform.
Figure 9B:
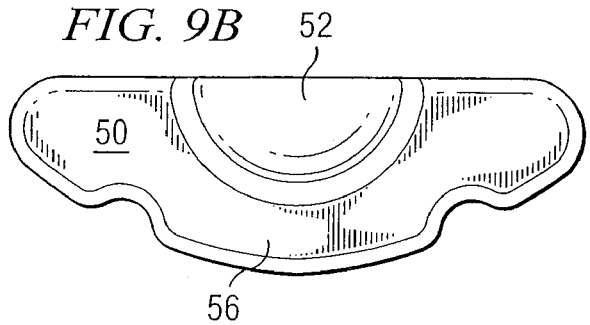

FIGS. 9A and 9B illustrate an example lower platform 50. In one embodiment, lower platform 50 includes a flat arched anterior portion 56 that seats on the user's lower anterior teeth, providing improved balance, decreased wear, and better overall comfort and performance.

Figure 10:
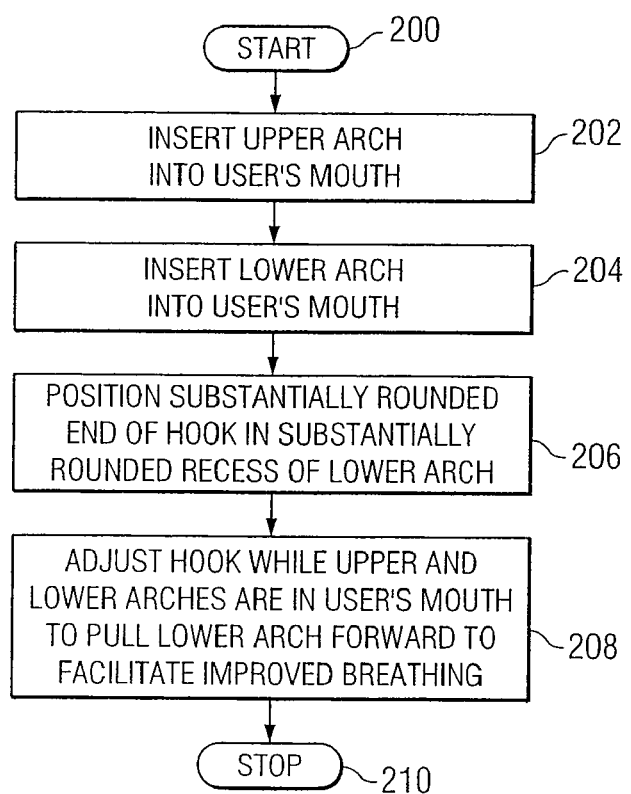
FIG. 10 illustrates an example method of improving a user's breathing.

FIG. 10 illustrates an example method of improving a user's breathing using device 100. The method begins at step 202, when upper arch 10 is inserted into the user's mouth. In one embodiment, upper arch 10 is adapted to receive at least some of the user's upper teeth and is coupled to hook 60 having a substantially rounded end 62. At step 204, lower arch 20 is inserted into the user's mouth. In one embodiment, lower arch 20 is adapted to receive at least some of the user's lower teeth, lower arch 20 having a substantially rounded recess 52 adapted to receive and position the substantially rounded end 62 of hook 60 to pull lower arch 20 forward to facilitate improved breathing. At step 206, the substantially rounded end 62 of hook 60 is positioned in the substantially rounded recess 52 of lower arch 20. At step 208, hook 60 is adjusted while upper arch 10 and lower arch 20 are in the user's mouth. As described above, although a substantially rounded end 62 and a substantially rounded recess 52 are primarily described and may be preferred in certain circumstances, the present invention contemplates any suitable cooperating shapes for end 62 and recess 52 depending on the embodiment.

Although an example method is described, the steps may be accomplished in any appropriate order. For example, inserting the upper and lower arches can be accomplished sequentially, in any order, or simultaneously. The present invention contemplates using methods with additional steps, fewer steps, or different steps, so long as the methods remain appropriate for improving a user's breathing.

Although the present invention has been described above in connection with several embodiments, it should be understood that numerous changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving a user's breathing, comprising:
   an upper arch adapted to receive at least some of the user's upper teeth, the upper arch having a midline that aligns substantially with the mesial plane of the user's mouth when the upper arch is inserted in the user's mouth;
   a hook coupled to the upper arch proximate the midline of the upper arch, the hook comprising an end having an anterior surface adapted to be directed in an anatomically anterior direction when the upper arch is inserted in the user's mouth; and
   a lower arch:
      adapted to receive at least some of the user's lower teeth;
      having a midline that aligns substantially with the mesial plane of the user's mouth when the lower arch is inserted in the user's mouth;
      having a lingual surface adapted to be positioned lingual to the user's lower teeth when the lower arch is inserted in the user's mouth; and
      comprising a recess in the lingual surface of the lower arch proximate the midline of the lower arch, the recess having a posterior surface adapted to be directed in an anatomically posterior direction when the lower arch is inserted in the user's mouth, the recess adapted to receive and position the end of the hook such that the anterior surface of the end of the hook contacts the posterior surface of the recess to pull the lower arch forward in the anatomically anterior direction to facilitate improved breathing.

2. The device of claim 1, wherein the recess of the lower arch is adapted to precisely position the end of the hook vertically relative to the upper arch to precisely determine an opening of the user's lower jaw.

3. The device of claim 1, wherein the recess comprises an elongated recess having a slightly larger height than the end of the hook and a significantly larger width than the end of the hook such that the lower arch is permitted substantially more lateral freedom of movement than vertical freedom of movement.

4. The device of claim 1, wherein:
   the hook comprises an arm having a length that determines an opening of the user's lower jaw; and
   the hook is selected from among multiple hooks having different arm lengths.

5. The device of claim 1, further comprising:
   an upper platform coupled to the upper arch, the upper platform comprising a slot adapted to receive and engage a flange of the hook, the slot further adapted to permit forward and rearward travel of the hook within the slot and to substantially prevent lateral and vertical movement of the hook relative to the upper platform; and
   a threaded adjustor disposed in a first channel formed in the upper platform, the adjustor adapted to engage a second threaded channel formed in the hook such that rotation of the adjustor causes the hook to travel forwardly or rearwardly within the slot.

6. The device of claim 5, wherein the upper platform further comprises a stop at each end of the first channel, the stops adapted to substantially prevent the adjustor from moving forwardly or rearwardly within the first channel.

7. The device of claim 5, wherein the adjustor comprises a screw having a recess adapted to receive an end of a tool for rotating the adjustor.

8. The device of claim 5, wherein the upper arch comprises a slot adapted to receive and engage the upper platform such that the slot and upper platform cooperate to substantially prevent movement of the upper platform within the slot of the upper arch.

9. The device of claim 5, further comprising one or more stops positioned in the upper platform and extending into a recess formed in the hook, the stops adapted to limit travel of the hook within the slot, an end of the recess formed in the hook contacting a stop preventing further travel of the hook within the slot in a corresponding direction.

10. The device of claim 9, wherein the one or more stops comprise a forward stop for limiting rearward travel of the hook within the slot and a rearward stop for limiting forward travel of the hook within the slot.

11. The device of claim 1, further comprising a lower platform coupled to the lower arch, the lower platform comprising the recess and a flat arched anterior portion that is forward of the recess and is adapted to seat on the user's lower anterior teeth.

* * * * *